(12) United States Patent
Zuelli et al.

(10) Patent No.: US 6,265,180 B1
(45) Date of Patent: Jul. 24, 2001

(54) NANOEMULSIONS FOR DELIVERING LIPOPHILIC SUBSTANCES INTO CELLS

(75) Inventors: Fred Zuelli, Küttigen; Franz Suter, Doettingen, both of (CH)

(73) Assignee: Mibelle AG Cosmetics, Buchs (CH)

( * ) Notice: Subject to any disclaimer, the term of this patent is extended or adjusted under 35 U.S.C. 154(b) by 0 days.

(21) Appl. No.: 09/262,516

(22) Filed: Mar. 4, 1999

(30) Foreign Application Priority Data

Mar. 30, 1998 (CH) .................................................... 0748/98

(51) Int. Cl.[7] .............................. C12Q 1/02; C12P 1/00; C12P 21/06; C12N 5/00; C12N 1/00
(52) U.S. Cl. ............................. 435/29; 435/29; 435/41; 435/69.1; 435/71.1; 435/134; 435/325; 435/375; 435/377; 435/404; 435/405; 435/243; 435/244
(58) Field of Search ............................... 435/29, 32, 243, 435/404, 325, 375, 377, 405, 244, 134, 41, 69.1, 71.1; 424/455

(56) References Cited

U.S. PATENT DOCUMENTS

| | | | |
|---|---|---|---|
| 5,152,923 | * 10/1992 | Weder et al. | 252/312 |
| 5,658,575 | * 8/1997 | Ribier et al. | 424/401 |

* cited by examiner

*Primary Examiner*—David M. Naff
(74) *Attorney, Agent, or Firm*—Tarolli, Sundheim, Covell, Tummino & Szabo L.L.P.

(57) ABSTRACT

Sterile nanoemulsions are prepared containing oily droplets of a diameter of less than 100 nm in an aqueous phase. The oily droplets contain a lipophilic substance, and have on their surface an amphoteric emulsifier in an amount of preferably 0.65 to 0.75 parts by weight amphoteric emulsifier for one part by weight of oily component forming the droplets. The oily component of the droplets is preferably a triglyceride containing oleic acid and/or linoleic acid. The nanoemulsions are used for delivering into cells the lipophilic substance contained by the oily droplets. This delivery can be used to biotransform the lipophilic substance, promote cell differentiation, growth or biosynthesis of a desired substance, or to test for toxicity of the lipophilic substance.

3 Claims, 5 Drawing Sheets

NANOEMULSIONS FOR DELIVERING LIPOPHILIC SUBSTANCES INTO CELLS

FIELD OF THE INVENTION

This invention relates to methods for determining the biocompability of lipophilic substances in cell culture test, and to nanoemulsions suitable in said methods.

BACKGROUND OF THE INVENTION

Nanoemulsions, alternatively called nanoparticles, are composed of oil particles, the surfaces of which are occupied by an amphoteric emulsifier in aqueous dispersions. They can be prepared by mixing triglycerides or fatty acid esters in aqueous phase using a high pressure homogenizer (EP-B1-0 406 162—H. G. Weder).

So far, they were used for the manufacture of pharmaceutical and/or cosmetic preparations, and also for the preparation of nutrient solutions in which the nanoemulsions serve as the energy supplier in cell cultures (EP-B1-0 406 162—H. G. Weder).

The cell culture technique is a biological system having a very wide application. Controlled culturing of these cells is mainly used in immunology, in biotechnology, in toxicology, in gene technology, and in cell biology. In all said applications the interaction of substances with cells is of primary importance. The exchange of biochemical substances with the cells takes place in the culture medium which is composed of a large number of different substances. In order to create ideal conditions for the cells, in most cases blood serum is added to the culture medium. However, for many uses the complementation of said medium with blood serum shows severe disadvantages, since the blood serum has an undefined composition, is expensive, and may contain undesired components, such as viruses, prions and germs. Therefore, for many applications the creation of so-called serum-free media is of primary importance.

Working with cell cultures, a general difficulty is the application of test substances which are insoluble in water. If possible, lipophilic substances are dissolved in alcohol or dimethylsulfoxide, and then added to the culture medium. However, this results in undefined dispersions of said substances having a low bioavailability. The use of solubilizers, such as Tween 20®, results in unstable and very toxic emulsions.

Therefore, no reliable and simple methods were so far available to solve the following problems:
- testing the biocompability of lipophilic substances in cell culture assays;
- testing the toxicity and/or the genotoxicity of lipophilic substances in cell culture assays;
- biotransformation of lipophilic substances in cell cultures;
- promotion of cell differentiation in primary cell cultures;
- separation of cells from lipids which were not incorporated;
- adaptation of cells from a complete medium to a serum-free medium;
- completion of cell culture media with lipophilic substances promoting cell growth;
- completion of cell culture media with lipophilic substances promoting biosynthesis of desired substances within the cells;
- defined and reproducible transport of lipophilic substances into the cells of cell cultures.

OBJECTS OF THE INVENTION

It is the primary object of the invention to solve the above mentioned problems by creating methods for delivering lipophilic substances to cell cultures, which lipophilic substances are to be tested in said cell cultures, by using nanoemulsions as vehicle.

The foregoing and further objects, advantages and features will be apparent from the following specification.

SUMMARY OF THE INVENTION

To meet these and other objects, the invention provides the following methods, and the following dispersions suitable for use in these methods:

a method of delivering a lipophilic substance into the cells of a cell culture, in a defined and reproducible manner, said method comprising the steps of: (a) preparing a dispersion consisting of a nanoemulsion containing said lipophilic substance, in aqueous phase; and (b) adding said dispersion to said cell culture, and optionally the further step of: (c) separating said cells from lipids which were not incorporated, by centrifugation and washing;

a method of testing the biocompatibility of a lipophilic substance in a cell culture assay, said method comprising the steps of: (a) preparing a dispersion consisting of a nanoemulsion containing said lipophilic substance to be tested, in aqueous phase; and (b) adding said dispersion to said cell culture, said test preferably being made on lipids used in the manufacture of cosmetics;

a method of testing the toxicity and/or the genotoxicity of a lipophilic substance in a cell culture assay, said method comprising the steps of: (a) preparing a dispersion consisting of a nanoemulsion containing said lipophilic substance to be tested, in aqueous phase; and (b) adding said dispersion to said cell culture;

a method of biotransforming a lipophilic substance by means of a cell culture, said method comprising the steps of: (a) preparing a dispersion consisting of a nanoemulsion containing the substance to be biotransformed, in aqueous phase; (b) adding said dispersion to said cell culture; and (c) collecting the biotransformed substance from said cell culture;

a method of promoting cell differentiation in a primary cell culture, said method comprising the steps of: (a) preparing a dispersion consisting of a nanoemulsion containing a substance able to promote cell differentiation, in aqueous phase; and (b) adding said dispersion to said cell culture;

a method of completing a cell culture medium with a lipophilic substance promoting the growth of cells by weight, said method comprising the steps of: (a) preparing a dispersion consisting of a nanoemulsion containing the substance promoting the growth of cells, in aqueous phase; and (b) adding said dispersion to said cell culture;

a method of completing a cell culture medium with a lipophilic substance promoting the biosynthesis of desired substances within the cells, said method comprising the steps of: (a) preparing a dispersion consisting of a nanoemulsion containing the substance promoting said biosynthesis, in aqueous phase; and (b) adding said dispersion to said cell culture;

a sterile dispersion useful for delivering a lipophilic substance into the cells of a cell culture, said dispersion consisting of a nanoemulsion, in aqueous phase, the oily particles of said dispersion containing said lipophilic substance to be delivered, and the surface of said oily particles being occupied by a non-toxic amphoteric emulsifier, wherein said oily component in which said lipophilic substance is dissolved preferably has such a low toxicity for said the cell culture that its growth is reduced for less than 20% as compared to a reference culture containing no oily component;

a sterile dispersion useful for testing a lipophilic substance by means of a cell culture, said dispersion consisting of a nanoemulsion, in aqueous phase, the oily particles of said dispersion containing said lipophilic substance to be tested, and the surface of said oily particles being occupied by a non-toxic amphoteric emulsifier, wherein said oily component in which said lipophilic substance is dissolved preferably has such a low toxicity for said cell culture that its growth is reduced for less than 20% as compared to a reference culture containing no oily component.

Preferably, said dispersions comprise as oily component a triglyceride of the fatty acids C 18:1 (oleic acid) and/or C 18:2 (linoleic acid), and comprise nanoemulsions comprising from 0.65 to 0.75 parts by weight of said amphoteric emulsifier for one part by weight of said oily component.

BRIEF DESCRIPTION OF THE DRAWINGS

Other characteristics and advantages of the invention will appear from the description which follows, given by way of example and with reference to the attached drawings in which.

DESCRIPTION OF THE PREFERRED EMBODIMENTS

Figure 1:
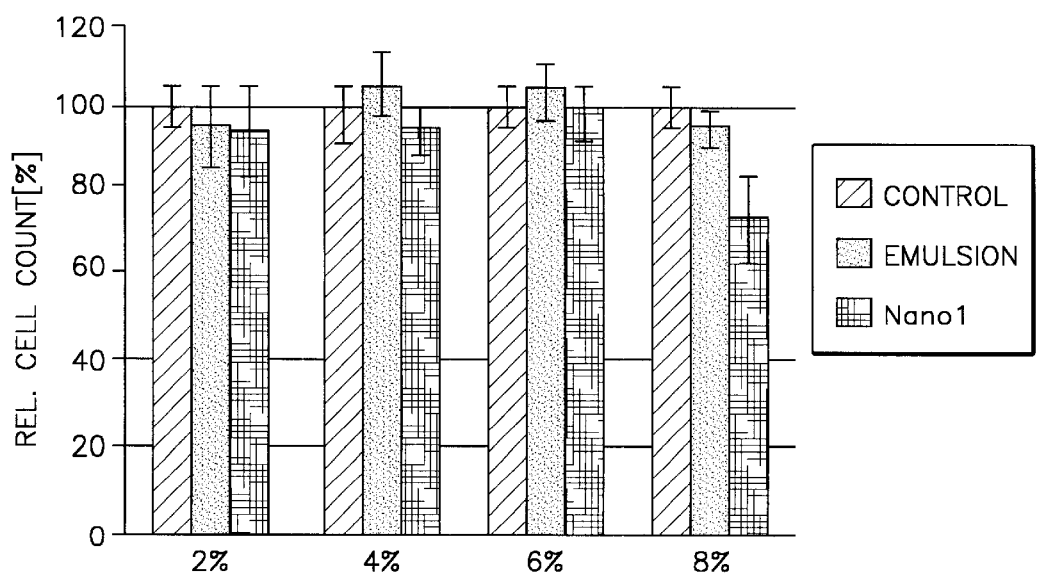
FIG. 1 is a representation of the relative cell number as a function of different concentrations of Nanoemulsion 1 ("Nano 1" of Example 1 and liposomes comprising the emusifier "Emul"). These relative cell numbers are compared with untreated cultures ("Kontr" is 100%).

Nanoemulsions useful in the present invention can easily be prepared by mixing the ingredients together and passing the mixture trough a high pressure homogenizer.

Preferably, the oily particles of the nanoemulsion have a diameter of less than 100 nm, and particularly of less than 40 nm, and preferably their surface is bearing the amphoteric emulsifier as a monolayer.

Preferably, the nanoemulsions have a negative zeta-potential, particularly between −10 mV and −50 mV, and especially between −30 mV and −40 mV. However, for special applications nanoemulsions having a positive zeta-potential may be advantageous. Such cationic nanoemulsions can e.g. be obtained by addition of a C8- to C22-alkylamine.

Preferably, the nanoemulsions contain more than 0.4 parts by weight, and particularly 0.45 to 0.75 parts by weight, of the ampotheric emulsifier per one part by weight of oil. As a general rule, the diameter of the oil particles increases as the portion of the amphoteric emulsifier decreases.

Preferably, the amphoteric emulsifier itself has a low toxicity to cell cultures, and preferably lecithin is used for this purpose.

Preferably, the oil phase as well has a low toxicity to cell cultures, and particularly such a low toxicity that the growth of the cell culture is reduced for less than 20% as compared to a reference culture containing no oily component.

Particularly useful for this purpose are natural triglycerides, and especially natural triglycerides of the fatty acid C 18:1 (oleic acid) and/or the fatty acid C 18:2 (linoleic acid). Said fatty acid have a very low toxicity and are particularly useful as solvent for lipophilic test substances.

As said above, the nanoemulsions can be prepared by high pressure homogenization of premixes of the ingredients. Preferably, the ratio of lecithin to oil is higher than 0.41. Optimal mixtures e.g. have a ratio of 0.6. Furthermore, it is of great advantage if the nanoemulsions have a small particle diameter. Oil-in-water emulsions comprising oil droplets which are smaller than 70 nm are transparent. Such transparent nanoemulsions facilitate visual control of the cell cultures. Moreover, dispersions of a small average particle size (e.g. 100 nm) can easily be sterilized by filtration.

Nanoemulsions are very stable and can be stored in a refrigerator for months before being added to the cell cultures.

Preferred embodiments of the invention are described and explained in the following examples and the annexed drawings.

EXAMPLES

Example 1

Treatment of TK6-lymphoblastoid Cells with a Nanoemulsion having a Low Toxicity

TK6-cells were cultivated in a RPMI-1640 medium, which was completed with 2 mmol of glutamine, 5% of gentamycin and 10% of horse serum. The cell suspension was inoculated into new cell culture flasks every 2 to 3 days. The number of cells was determined by means of a Neubauer chamber. The influence of Nanoemulsion 1 and of the void lecithin particles (liposomes) on the cell growth was determined for different concentrations after 2 days.

FIG. 1 shows the relative cell numbers compared to untreated cells ("Contr" is 100%). Nanoemulsion 1 ("Nano 1") has no influence on the cell growth up to a concentration of 6%. The emulsifier ("Emul") has even no influence on the relative cell number up to a concentration of 8%.

Figure 2:
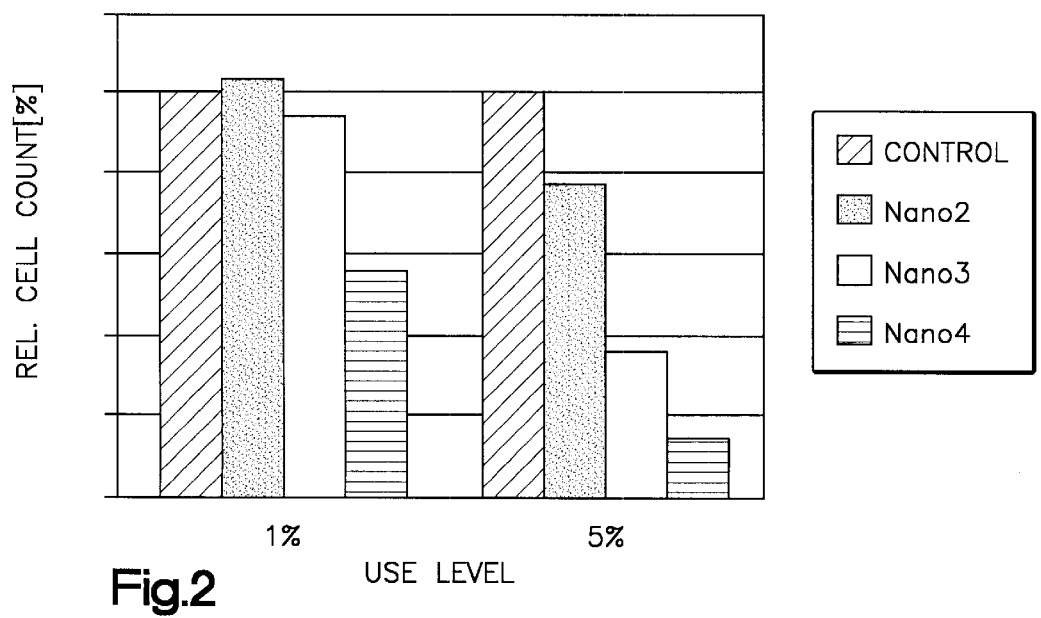
FIG. 2 is a representation of the relative cell number as a function of various amounts of three different nanoemulsions ("Nano 2", "Nano3", and "Nano 4" of Example 1). These relative cell numbers are compared with untreated cultures ("Kontr" is 100%).

FIG. 2 shows that nanoemulsions comprising other oil components are essentially more toxic than the oil in Nanoemulsion 1 when using the same concentration and the same emulsifier. In FIG. 2, the oil components are sunflower oil ("Nano 2"), hydrogenated peanut oil ("Nano 3"), and a saturated C 8/10 triglyceride ("Nano 4").

| Composition of Nanoemulsion 1 | |
|---|---|
| Lecithin | 0.6% |
| Triglyceride | 1.0% |
| of which: | 90% C 18:1 and 10% C 18:2 |
| Particle diameter | 41 nm |

| Composition of Nanoemulsion 2 | |
|---|---|
| Lecithin | 0.6% |
| Sunflower oil | 1.0% |
| Particle diameter | 45 nm |

| Composition of Nanoemulsion 3 | |
|---|---|
| Lecithin | 0.6% |
| Hydrogenated peanut oil | 1.0% |
| Particle diameter | 50 nm |

| Composition of Nanoemulsion 4 | |
|---|---|
| Lecithin | 0.6% |
| Caprylic acid/capric acid triglyceride | 1.0% |
| Particle diameter | 45 nm |

Example 2

Controlled Delivery of an UV filter into TK6-lymphoblastoid Cells by Means of a Nanoemulsion TK6-cells were cultivated in a RPMI-1640 medium, which was completed with 2 mmol of glutamine, 5% of gentamycin and 10% of horse serum. 1%, 5%, and 10%, respectively, of Nanoemulsion 5 were added to the cell suspension ($7 \times 10^5$ cells/ml). After an incubation time of 10 minutes 10 ml each of the culture were centrifuged, and the cells were washed twice with 10 ml of buffer. The amount of UV filter in the cells was determined after extraction with chloroform by measuring the absorption (Table 1). Using Nanoemulsion 5, defined amounts of UV filter could be delivered into the cells.

TABLE 1

| 1% Nanoemulsion 5 | 10 µg UV filter/$7 \times 10^6$ cells |
| 5% Nanoemulsion 5 | 39 µg UV filter/$7 \times 10^6$ cells |
| 10% Nanoemulsion 5 | 51 µg UV filter/$7 \times 10^6$ cells |

The uptake of the nanoparticles into the cells is time-dependent.

Figure 3:
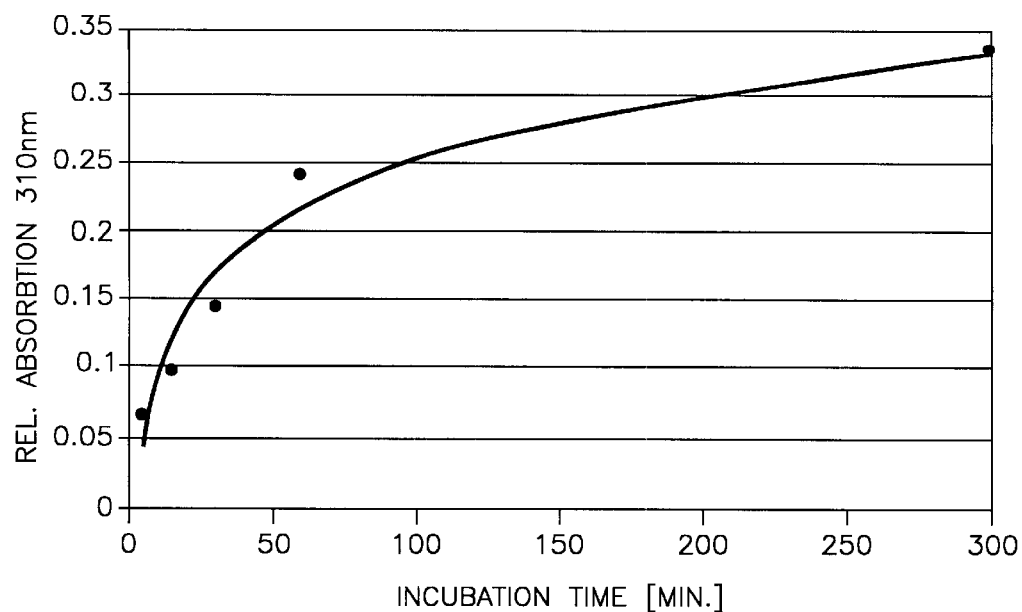
FIG. 3 is a representation of the time-depending course of the delivery of UV filters into cells which were incubated with Nanoemulsion 5 of Example 2. The delivery of UV filters into cells is measured as relative absorption at 310 nm of extracted cells.

FIG. 3 shows the time-depending course of the uptake of UV filters into the cells. $2 \times 10^5$ cells/ml were incubated with 2% of Nanoemulsion 5. After 5, 15, 30, 60, and 300 minutes, respectively, 10 ml each of the cell culture were centrifuged. The cells were washed twice with 10 ml of buffer and then extracted with chloroform. The relative concentrations of UV filter in the various extracts are shown in FIG. 3.

In contrast to this, the uptake of the UV filter isoamyl-methoxyzinnamate into TK6-cells from a medium containing 2% of a 0.5% alcoholic solution of the UV filter was totally undefined, since the cells cannot be properly separated from the UV filter dispersion (Table 2).

TABLE 2

| Incubation time | Rel. absorption 310 nm |
|---|---|
| 5 min | 1.0 |
| 5 min | 1.1 |
| 30 min | 1.0 |
| 60 min | 0.9 |
| 240 min | 1.0 |
| Control without cells | 0.7 |

| Composition of Nanoemulsion 5 | |
|---|---|
| Lecithin | 0.6% |
| Triglyceride | 0.5% |
| of which: | 90% C 18:1 and 10% C 18:2 |

| Composition of Nanoemulsion 5 | |
| --- | --- |
| Isoamyl-methoxyzinnamate 4-(4-Methoxyphenyl)-2-propionic acid-3-methylbutyl-ester | 0.5% |
| Particle diameter | 49 nm |

Example 3

Controlled Delivery of an UV Filter into Fibroblasts and TK6-lymphoblastoid Cells by Means of a Nanoemulsion The TK6-cells were cultivated as described in example 1. The fibroblasts (Normal Human Dermal Fibroblasts) were cultivated in a serum-free medium (PromoCell®). 2% of Nanoemulsion 6 were added to the cultures, and after one hour the amount of incorporated UV filter was determined in the same manner as described in example 2 (Table 3).

| Composition of Nanoemulsion 6 | |
| --- | --- |
| Lecithin | 0.6% |
| Triglyceride | 0.9% |
| of which: | 90% C 18:1 and |
|  | 10% C 18:2 |
| Butyl-methoxydibenzoyl-methane 1-(4-Methoxyphenyl)-3-(4-tert-butyl-phenyl)-3-hydroxy-2-propen-1-on | 0.1% |
| Particle diameter | 50 nm |

TABLE 3

| TK6-Lymphoblastoid cells Amount of UV filter | Fibroblasts (NHDF) Amount of UV filter |
| --- | --- |
| 1,43 µg UV filter/2.0 × $10^6$ cells | 1,15 µg UV filter/1.0 × $10^5$ cells |

Example 4

Determining the Toxicity of UV Filters on TK6-lymphoblastoid Cells

Figure 4:
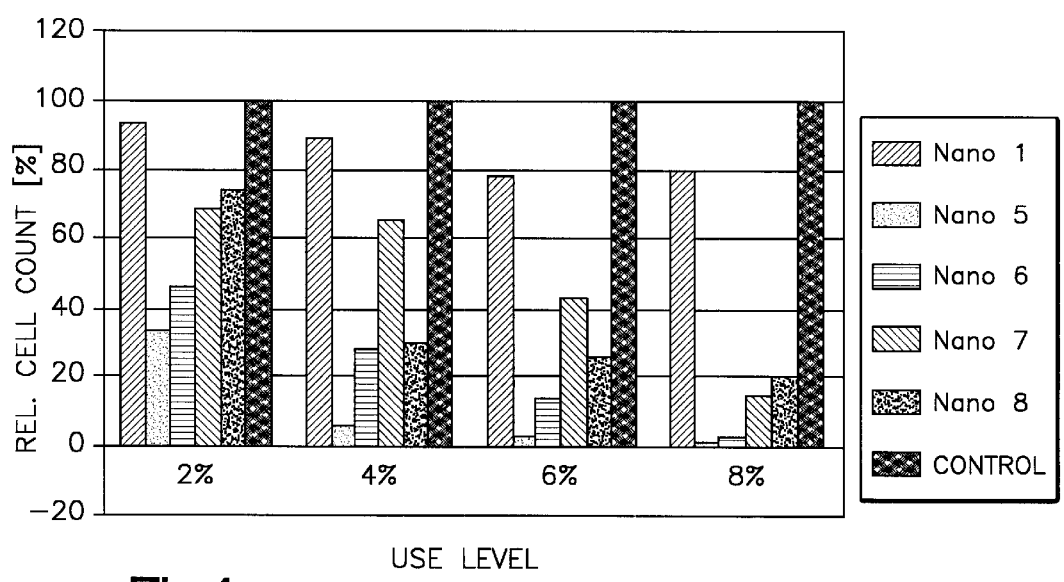
FIG. 4 is a representation of the relative cell numbers as a function of various amounts of five different nanoemulsions ("Nano 1", "Nano 5", "Nano 6", "Nano 7", and "Nano 8" of Examples 1, 2, 3, and 4, respectively). These relative cell numbers are compared with untreated cultures ("Kontr" is 100%).

The TK6-cells were cultivated in a RPMI-1640 medium as described in example 1. The number of cells was determined by means of a Neubauer chamber. The influence of Nanoemulsions 5, 6, 7 and 8 comprising encapsulated UV filters and of Nanoemulsion 1 comprising no UV filter was determined at various concentrations after 2 days. FIG. 4 shows the relative cell numbers as compared to untreated cells (control is 100%). The toxicity of the different UV filters is varying and depends on the concentration used.

| Composition of Nanoemulsion 7 | |
| --- | --- |
| Lecithin | 0.6% |
| Triglyceride | 0.9% |
| of which: | 90% C 18:1 and |
|  | 10% C 18:2 |

| Composition of Nanoemulsion 7 | |
| --- | --- |
| Isoamyl-methoxyzinnamate (4-(4-Methoxyphenyl)-2-propionic acid-3-methylbutyl-ester) | 0.1% |
| Particle diameter | 60 nm |

| Composition of Nanoemulsion 8 | |
| --- | --- |
| Lecithin | 0.6% |
| Triglyceride | 0.9% |
| of which: | 90% C 18:1 |
|  | 10% C 18:2 |
| Benzophenon (2-Hydroxy-4-methoxy-benzophenone) | 0,1% |
| Particle diameter | 60 nm |

Example 5

Figure 5:
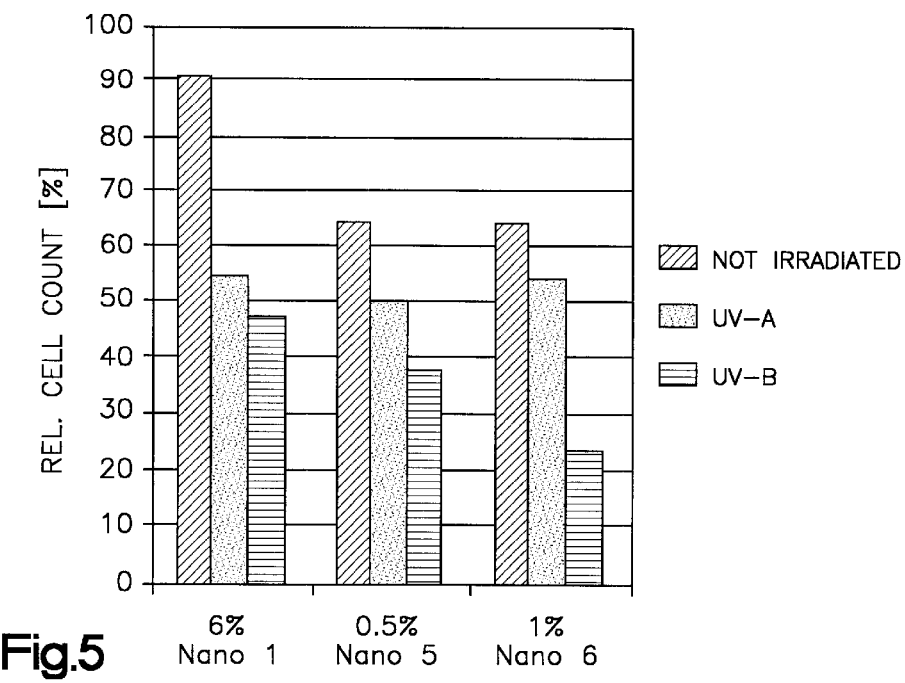
FIG. 5 is a representation of the relative cell number as a function of various amounts of three different nanoemulsions ("Nano 1", "Nano 5", and "Nano 6" of Examples 1, 2, and 3, respectively) which were subjected to UV-A and UV-B irradiation. The relative cell numbers of the UV treated nanoemulsions are compared with the corresponding untreated nanoemulsions ("not irradiated").

Determination of the Toxicity of UV Filters which have been Subjected to UV Irradiation The TK6-cells were cultivated in a RPMI-1640 medium as described in example 1. The number of cells was determined by means of a Neubauer chamber. The influence of Nanoemulsions 5 and 6 comprising encapsulated UV filters and of Nanoemulsion 1 comprising no UV filter was determined before and after UV-A and UV-B1 irradiation of said nanoemulsion (FIG. 5).

Example 6

Figure 6:
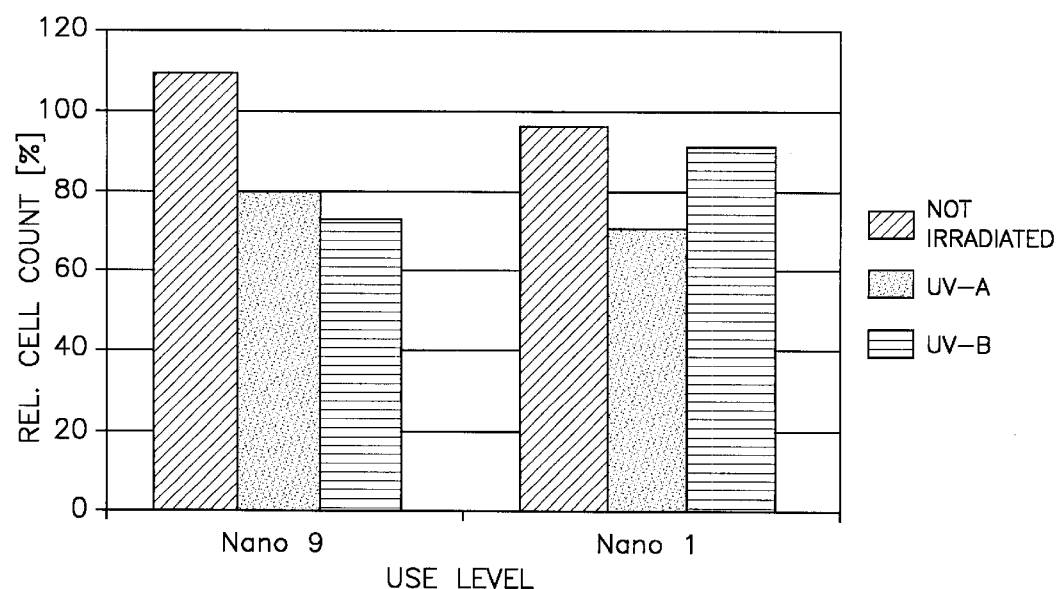
FIG. 6 is representation of the relative cell number as a function of the application of two different nanoemulsions ("Nano 1" and "Nano 9" of Examples 1 and 6, respectively) subjected to UV-A and UV-B irradiation. The relative cell numbers of the UV treated nanoemulsions are compared to the corresponding untreated nanoemulsions ("ni").

Determination of the Toxicity of Cosmetic Lipids Filters which have been Subjected to UV Irradiation The TK6-cells were cultivated in a RPMI-1640 medium as described in example 1. The number of cells was determined by means of a Neubauer chamber. The influence on the cells of Nanoemulsion 9 comprising encapsulated polyunsaturated fatty acids (linolenic acid) and of Nanoemulsion 1 was determined before and after UV-A and UV-B irradiation of said nanoemulsions (FIG. 6).

| Composition of Nanoemulsion 9 | |
| --- | --- |
| Lecithin | 0.6% |
| Triglyceride | 0.8% |
| of which: | 90% C 18:1 and |
|  | 10% C 18:2 |
| Borage oil | 0.2% |
| Particle diameter | 60 nm |

Example 7

Determination of the Genotoxicity of Used Frying Oil

The mutagenicity rate of genotoxic substances can be determined e.g. in CHO-cells (Chinese Hamster Ovary Cells) having suitable selectable purine or pyrimidine auxotrophies. The genotoxicity of used frying oil can be determined by encapsulating it in a suitable nanoemulsion (e.g. Nanoemulsion 10).

| Composition of Nanoemulsion 10 | |
| --- | --- |
| Lecithin | 0.7% |
| Frying oil | 1.0% |
| Particle diameter | 85 nm |

Example 8

Determination of the Neurotoxicity of Pesticides and Herbicides

The specific neurotoxicity of lindan (γ-1,2,3,4,5,6-Hexachlorocyclohexane) can be determined in vitro through incubation of CHEN-cells (Chick Embrio Neural Cells) with a suitable nanoemulsion comprising encapsulated lindan (e.g. Nanoemulsion 11) without encountering solubility problems.

| Composition of Nanoemulsion 11 | |
| --- | --- |
| Lecithin | 0.38% |
| Caprylic acid/capric acid triglyceride | 0.81% |
| Lindan | 0.09% |
| (γ-1,2,3,4,5,6-Hexachlorocyclohexane) | |
| Particle diameter | 75 nm |

Example 9

Determination of the Neurotoxicity of Drugs

The specific neurotoxicity of Valium® (Diazepam) can easily be determined in a concentration dependent mode in vitro through incubation of CHEN-cells (Chick Embrio Neural Cells) with a suitable nanoemulsion comprising encapsulated Valium® (e.g. Nanoemulsion 12).

| Composition of Nanoemulsion 12 | |
| --- | --- |
| Lecithin | 3.32% |
| Caprylic acid/capric acid triglyceride | 7.20% |
| Valium ® | 0,36% |
| (7-Chloro-1-methyl-5-phenyl-1,4-benzodiazepin-2-on) | |
| Particle diameter | 80 nm |

Example 10

Biotransformation of Hormone Precursors in Cell Cultures

In biotechnology, complex chemical molecules, e.g. hormones, can easily be prepared by means of cell cultures. Thus, precursors of said molecules can be added to the culture medium. In the cells, the precursors are transformed by specific enzymes and then again released into the culture medium. By means of nanoemulsions, lipophilic educts can efficiently be delivered into these cells. The encapsulated educts can then easily be separated form the products released to the culture medium by simple separation methods, such as dialysis or "Cross-Flow" ultrafiltration. 17-Hydroxyprogesterone, e.g., can be delivered into the interstitial cells of testical tissue cultures in a controlled way. Said substance is transformed in said cells into 5-α-Androstane-17-β-ol-3-one which is than again released to the culture medium.

Example 11

Promotion of Cell Differentiation of Primary Cutaneous Keratinocytes by Means of Nanoemulsions Embryonic porcine cutaneous keratinocytes were cultivated in M199-medium containing 10% of serum and 0.4 μg/ml hydrocortisone. By addition of 1% of Nanoemulsion 13 to the culture medium the differentiation of the keratinocytes was improved.

| Composition of Nanoemulsion 13 | |
| --- | --- |
| Lecithin | 0.6% |
| Caprylic acid/capric acid triglyceride | 0.6% |
| Vitamin E acetate | 0.3% |
| Vitamin A palmitate | 0.1% |
| Particle diameter | 45 nm |

Example 12

Figure 7:
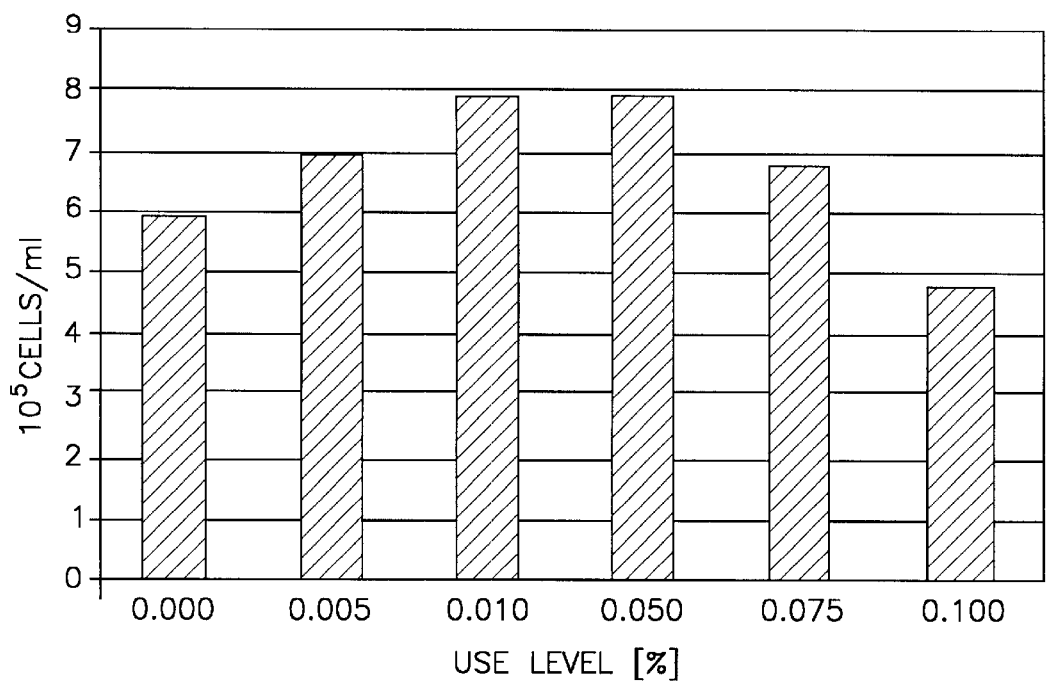
FIG. 7 is a representation of the number of cells per ml as a function of the addition of different amounts of nanoemulsion 13 of Example 11 to the culture medium.

Use of a Nanoemulsion Containing Vitamins A and E for Completing a Serum-free Cell Culture Media in Order to Promote Cell Growth Hybridoma cells producing a specific antibody were cultivated in an serum-free medium (Cell Culture Technologies). Cell growth could be improved by the addition of Nanoemulsion 13 (FIG. 7).

Example 13

Figure 8:
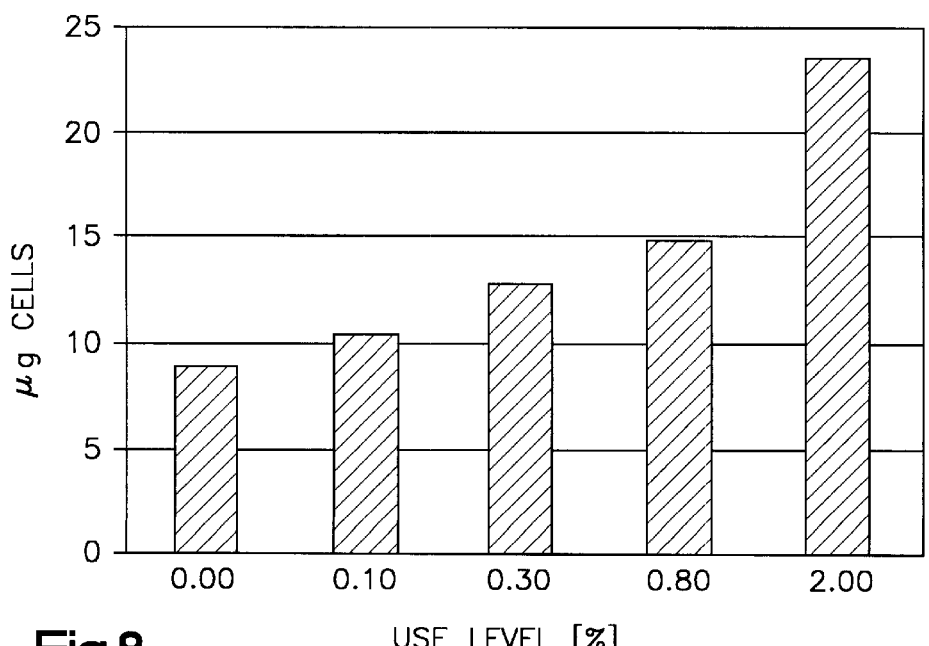
FIG. 8 is a representation of the amount of cells in microgram obtained in a culture which contained different amounts of nanoemulsion 13 of Example 11.

Completion of a Serum-free Cell Culture of Fibroblasts by a Nanoemulsion in Order to Increase the Biomass Production Balb-3T3 fibroblasts were cultivated in serum-free DMEM/F12-(1:1) medium (BioConcept) at various concentrations of Nanoemulsion 13. The 50 ml cultures were harvested after 9 days, and the biomass was determined (FIG. 8).

Example 14

Figure 9:
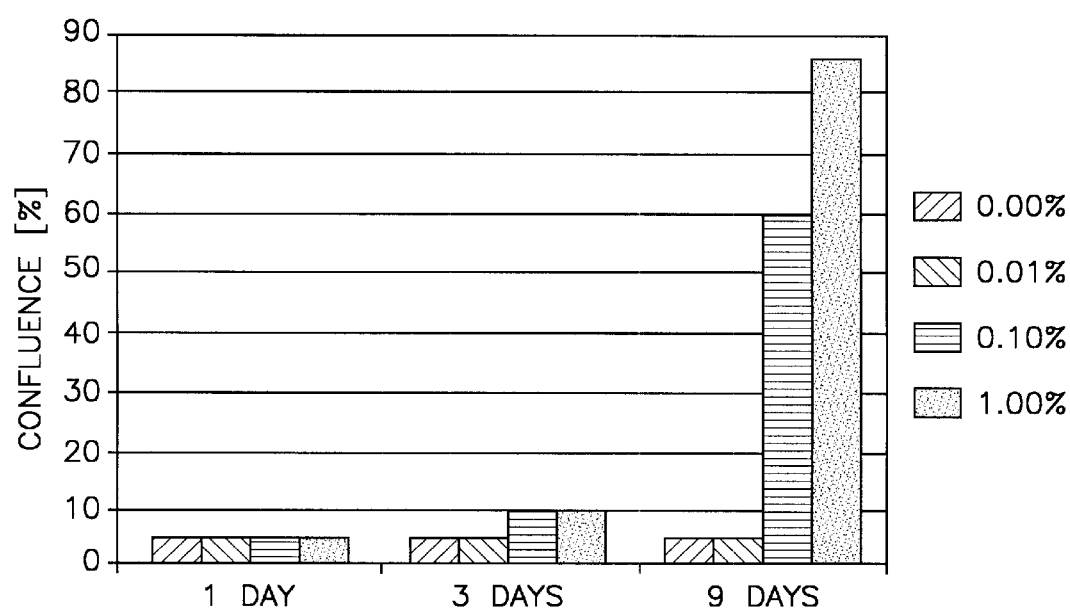
FIG. 9 is a representation of the growth adaptation of a fibroblast culture to a serum-free medium after the addition of various amounts of nanoemulsion 13 of Example 11. The growth was measured as percentage of confluence after different time periods.

Use of Nanoemulsions Containing Vitamins A and E for Adapting Fibroblasts to a Serum-free Medium 3T3-Fibroblasts were cultivated in DMEM/F12-(1:1) medium (BioConcept) containing 10% of serum. The confluent culture was trypsinized and inoculated into a serum-free DMEM/F12-(1:1) medium containing various concentrations of Nanoemulsion 13. Cell growth was determined after different time periods by estimating the confluence (FIG. 9).

Example 15

Use of Nanoemulsions Containing Unsaturated Fatty Acids, Vitamins and β-carotene in Order to Promote the Biosynthesis of Specific Antibodies in Hybridoma Cells in Serum-free Medium Serum-free media are particularly suitable for the production of proteins, since they do not contain any foreign proteins which could affect the isolation of the products.

However in serum-free cell cultures essential lipophilic substances, such as unsaturated fatty acids and vitamins, normally present in the serum are often lacking. These substances cannot be added without hesitation to the serum-free medium, since they are water-insoluble, difficult to be dispersed in a controlled manner, and show only a low bioavailability. By completing these media with nanoemulsions containing essential lipids (e.g. Nanoemulsion 14) e.g. the production of specific antibodies in hybridoma cells can be improved substantially.

| Composition of Nanoemulsion 14 | |
|---|---|
| Lecithin | 0.30% |
| Triglyceride | 0.50% |
| of which: | 90% C 18:1 and |
| | 10% C 18:2 |
| α-Tocopherol | 0.0100% |
| Vitamin A acetate | 0.0050% |
| Linoleic acid | 0.0100% |
| Linolenic acid | 0.0100% |
| β-Carotene | 0.0001% |
| Particle diameter | 65 nm |

Example 16

Use of Nanoemulsions for Promoting the Biosynthesis of Recombinant Proteins

CHO-cells (Chinese Hamster Ovary Cells) are often used for the production of recombinant proteins, such as growth factors, blood coagulation factors, and cytokines. Thereby, the biosynthesis of these products in serum-free media can be improved by addition of nanoemulsions containing essential lipophilic substances (e.g. Nanoemulsion 13.)

Example 17

Use of Nanoemulsions in Perfusion Systems

Nanoemulsion 13 can also be used for increasing the interferon-β secretion of fibroblasts which are cultivated in a perfusion system.

We claim:

1. A sterile, substantially non-toxic dispersion useful for delivering a lipophilic substance into cells of a cell culture and for testing a lipophilic substance by means of a cell culture, said dispersion being a nanoemulsion comprising:

a lipophilic substance and an oily component consisting of droplets dispersed in an aqueous phase, the oily droplets containing the lipophilic substance to be delivered, the surface of the oily droplets comprising a non-toxic amphoteric emulsifier, the oily droplets having a diameter of less than 100 nm, and the nanoemulsion comprising from 0.65 to 0.75 parts by weight of amphoteric emulsifier for one part by weight of the oily component.

2. The dispersion of claim 1, wherein said oily component is a low toxicity oil component, which reduces the cell culture's growth not more than 20% as compared with a reference cell culture containing none of the oily component.

3. The dispersion of claim 1 wherein the oily component is a triglyceride comprising fatty acids selected from the group consisting of oleic acid and linoleic acid.

* * * * *